United States Patent [19]

Mikoshiba et al.

[11] Patent Number: 6,087,483

[45] Date of Patent: *Jul. 11, 2000

[54] DNA CODING AN INOSITOL 1,4,5,-TRIPHOSPHATE BINDING PROTEIN

[75] Inventors: Katsuhiko Mikoshiba, Tokyo; Teiichi Furuichi, Aichi, both of Japan

[73] Assignee: Kyowa Hakko Kogyo Co., Ltd., Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/583,937

[22] Filed: Jan. 11, 1996

Related U.S. Application Data

[63] Continuation of application No. 08/228,004, Apr. 15, 1994, abandoned, which is a continuation of application No. 08/087,468, Jul. 8, 1993, abandoned, which is a continuation of application No. 07/793,277, Nov. 12, 1991, abandoned, which is a division of application No. 07/550,554, Jul. 10, 1990, abandoned.

[30] Foreign Application Priority Data

Dec. 14, 1989 [JP] Japan .................................. 1-324256

[51] Int. Cl.⁷ .................................................. C07H 19/00
[52] U.S. Cl. ..................... 536/22.1; 536/23.1; 435/252.1; 435/69.1; 435/71.1; 435/320.1
[58] Field of Search ................................. 536/22.1, 23.1; 435/252.1, 69.1, 71.1, 320.1

[56] References Cited

PUBLICATIONS

Nordquist et al Journal of Neuroscience 8:4780–4789, 1988.
Suggs et al PNAS 78:6613–6617, 1989.
Mignery et al Nature 342:192–195, 1989.
Takeshima et al, Nature 339:439–445, 1989.
Furuichi et al Nucleic Acids Res 17:5385–86 1989.
Maeda et al, Bulletin of the Japanese Neurochemical Society 27, 60–61, 1988 (Translation).
Snyder et al, Cell Calcium 10:337–342, 1989.
Young et al. PNAS 80:1194–1198, 1983.
Maeda et al, Developmental Biology 133:67–76, 1989.
Maeda et al, Journal of Neurochemistry 51:1724–1730 1988.
Maniatis et al 19882 Molecular Cloning Cold Spring Harbor Lab, Cold Spring Harbor NY.
Furuichi et al Nature 342:32–38 Nov. 1989.
Mignery et al J. of Biol Chem 265:12679–12685 Jul. 1990.
Nordquist et al J. Neurosci 1988 8:4780–4789 (Abst) Database Search.
Supattapone et al The J. of Biol. Chem. 263:1530–1534 1988.
Spat et al Nature vol. 319 Feb 1986 A Saturable receptor for P–inositol–1,4,5–trisphosphate in hepatocytes & neutrophils.
Worley et al J of Bio Chem vol. 262 1987 Characterization of an Inositol Trisphosphate Receptor Binding in Brain.

*Primary Examiner*—James C. Housel
*Assistant Examiner*—Jennifer Graser
*Attorney, Agent, or Firm*—Nixon & Vanderhye

[57] ABSTRACT

A polypeptide capable of binding to inositol 1,4,5-trisphosphate, a deoxyribonucleic acid (DNA) coding for said polypeptide, a recombinant plasmid harboring said DNA or a part thereof, a microorganism and animal cells each harboring said plasmid, and a method of producing said polypeptide.

7 Claims, 7 Drawing Sheets

```
MetSerAspLysMetSerSerPheLeuHisIleGlyAspIleCysSerLeuTyrAlaGluGlyPheIleSerThrLeuGlyLeuValAspAlaArgCysValGln                40
ProGluAlaGlyAspLeuAsnAsnProProLysLysPheArgAspCysLeuCysPheLysLeuCysProMetAsnArgTyrSerAlaGlnLysPheTrpLysAlaAlaLysProGlyAla      80
AsnSerThrThrAspAlaValLeuLeuAsnLysLeuHisIleHisAlaAlaLeuAlaAspLeuGlyLysLysGlnAsnArgLysLeuGluGlyThrValIleGlnTyrGlyAsnVal        120
IleGlnLeuLeuHisLeuLysSerAsnLysTyrLeuThrValAsnLysAlaMetArgValThrLeuAspGlyAlaAspGlyAsnGlyGlySerTrp                            160
PheTyrIleGlnProPheTyrLysLeuArgSerIleGlyTyrAspSerValValIleGlyAspLysValLeuAsnProValAsnAlaGlyGlnProLeuHisAlaAlaSerSerHisGlnLeu  200
ValAspAsnProGlyCysAsnGluValAsnSerValAsnCysAsnThrSerTrpLysIleValLeuPheMetLysTrpSerAspAsnLysSerAspAsnIleLeuLysGlyGlyAspValVal  240
ArgLeuPheHisAlaGlyGlnHisAlaAspProCysAspThrCysAspProLysPheLeuThrPheArgPheLysHisLeuHisIleValPheLeuArgThrGlyArgGlnSerAlaThrSerAlaThrSerLysAla  280
LeuTrpGluValGluValValGlnHisAspProCysArgGlyGlyGlyHisLeuAlaThrGlyHisIleTyrLeuAlaAlaGluValAlaAspPro                            320
AspPheGluGluGluCysLeuGlyPheGlnProSerValAlaSerArgSerArgLeuArgArgAsnAlaGlnGluLysValTyrSerLeuValSerValProGlu                   360
GlyAsnAspIleSerSerIleGluPheLeuAspThrThrLeuArgGlyGlyAspTyrValArgLeuArgHisLeuCysThrAsnThrTrpValHis                            400
SerThrAsnIleProIleAspLysGluGluGluProValMetLeuLysIleAlaGlyLySerIleAlaGlyLysLeuGluLysGlyThrIleGluThrGlnAsnGluArgArgSerValThrLysLeuLeuAspLeu 440
ArgAspLeuAspPheAlaAsnAspAlaSerLysValLeuGlySerIleAlaGlySerIleGluThrGlnAsnGluArgArgSerValThrLysLeuLeuAspLeu                    480
ValTyrPheValThrPheGlyThrAsnSerGlyHisIleGluLeuGlyGlnAspValLeuGluValValPheSerLysProAsnArgGluArgGlnLysLeuMetArgGluGlnLysIlePhe  520
LysLeuLeuGlnAlaProPheThrAspPheThrAspCysGlyAlaAspGlyProMetLeuArgLeuGluLeuAspGlnArgHisIleSerAlaProPheArgLeuCysArgLeuCysTyrArgValLeu            560
ArgHisSerGlnAsnGlnAspTyrArgLysAsnGlyGluTyrIleAlaAlaGluIleIleGlyPheMetGlnLysGlnIleIleGlyTyrAspValLeuAlaGluAspThrIleThrAlaLeuLeuHis            600
AsnAsnArgLysLeuGluLysHisIleIleThrAlaAlaGluIleGlyAspThrPheValSerLeuValArgLysAsnArgGluProArgPheLeuAspTyrLeuSerAspLeuCysValSer                 640
MetAsnLysSerIleProValThrGlnGlnAspGluLeuGlnAspValLeuAsnProThrAsnAlaAspIleAlaValLeuAsnProThrAsnAlaAspIleAlaLeuIleGluIleThrLysLeuGluThrLysSerAsnLysSerValLeuGluArgGluAlaGlnPheGluGlyVal  680
SerThrGlyGluAsnAlaLeuGlyAlaGlyIleAspArgAspIleLeuAspLeuIleLeuGluLeuIleGluThrLysSerAsnLysSerValLeuGluArgGluAlaGlnPheGluAspAlaLys            720
GlyGlnLysGluAspArgAspIleLeuGluSerTyrTyrArgGlnLeuAsnLeuPheAlaArgMetCysSerLeuAspArgGlnTyrLeuValAlaIleAsnGluIleSerGlyGlnLeuAsp                760
ValAspLeuIleLeuLeuArgCysMetSerSerAspGluAsnLeuProTyrAspLeuArgAlaSerPheLysArgLeuMetLeuHisIleMetHisValAspAspTyrProGlnValThrPro                800
ValLysTyrAlaArgLeuIleProSerGluIleAlaIleCysAspTyrAspSerSerGlyThrSerLysLysAspGluIleLeuLysGluLeuValAspArgPheAlaGlnThrMetGluPheVal            840
GluGluTyrLeuArgAspValCysGlnArgPheProPheSerAspLysSerGlnAsnArgPheGluValValAsnLeuAlaArgAsnLeuIleTyrPheGlyPheTyrAsn                            880
```

Fig. 2B

```
PheSerAspLeuArgLeuThrLysIleLeuLeuAlaIleLeuAspCysValHisValThrThrIlePheProIleSerLysMetThrLysGlyGluAsnLysGlySerAsnVal       920
MetArgSerIleIleIlsGlyValGlyValGlyLeuMetThrGlyGluLeuMetThrLysLeuLysIleIleIleGluIleLeuGlnPheIleLeuAsnValArgLeuAspTyrArgIleSerCysLeuLeuCysIlePheLysArgGlu    960
GluLysGluAspIleMetValMetAspIleMetAspIleMetAspIleMetAlaProGlyPheLeuProMetAlaAlaAlaProThrProMetAlaAlaAlaProTyrArgIleLeuAsnValArgLeuAspTyrArgIleSerCysLeuLeuCysIlePheLysArgGlu  1000
PheAspGluSerAsnSerGlnSerSerGlyThrSerSerGlyAsnSerSerGlyAsnSerGlyAsnGlnProGlyAlaLeuAspPheGluHisIleGluGluGlnAlaAlaGluGlyIle  1040
PheGlyGlySerGluGluAsnThrProLeuAspPheLeuArgValLeuLeuHisLeuThrMetHisAspTyrProProLeuValSerGlyAlaLeu  1080
GlnLeuLeuPheArgIleSerPheSerGlnArgGlnValLeuGlnAlaPheLysGlnValLeuGlnValLeuAspAsnTyrLysGlnIleLysGlnAspLeuAsp  1120
GlnLeuLeuArgSerIleValGluLysSerGluLysTrpValTyrLysGlyLeuGlnArgGlyIleGlnGlyProAspMetAspGluProMetAspSerGlyAlaSerGlyLeuHisLysLysThrGluGluGlyThrSer  1160
LysProLeuLysHisGluSerThrSerSerTyrArgValValLysGluLeuLeuArgLeuSerLeuCysValGluIleLysSerValArgLysSerArgLysGln    1200
GlnGlnArgLeuLeuArgAsnMetGlyAlaHisAlaValValLeuGluLeuGluHisLysIleIleProTyrGluLysAlaGluThrLysMetGlnIleValMetThrArgLeuAlaIleIleGluPhe    1240
LeuGlnAsnPheCysAlaGlyAsnGlnAsnGlnAlaLeuValAlaLeuLeuHisLysIleIleAsnLeuPheLeuLysProGlyIleIleLeuGluValAlaValThrMetGlnHisIlePheMetAsnAsn    1280
PheGlnLeuCysSerGluIleAsnGluArgValValAlaValGlnHisPheValLeuValPheTyrArgAsnValGlnTyrIleLeuPheLeuGlnThrLeuIleGlnMetMetArgSer    1320
LysPheIleLeuLysCysGlnAspMetValMetAlaGluLeuValPheTyrArgAsnAspAlaSerPheGlnAlaSerPheGlnThrLeuIleGlnMetMetArgSer    1360
GluArgAspAspArgMetAspPheLeuAsnSerProLeuMetTyrHisIleIleHisLeuValGluLysIleIleHisAsnPheLeuAsnHisCysTyrThrGluGlyIleLysCysAsnSerLeuLeu    1400
ProLeuAspAspAspIleValArgValThrHisGluLysCysIleProGluValLysIleCysTyrValAspThrGluIleLeuCysTyrHisIleAsnPheLeuAsnHisCysTyrThrGluGlyIleLysCysAsnSerLeuLeu  1440
TyrThrSerAsnHisMetTrpLysLeuPheGluAsnPheLeuValAspIleCysSerArgIleAlaCysAsnAsnThrSerArgAlaArgGlnProValPheValArgLysTyrValThrGlu    1480
IleValMetSerIleValThrThrPheThrPheSerSerProPheSerSerAspGlnProValPheValGlnLeuLeuGlnGlyValPheArgValTyrHis    1520
CysAsnTrpLeuMetProSerGlnLysValSerAlaSerValGlnLysCysIleArgValLeuSerCysIleArgLeuLeuAsnTrpProLeuLeuSerArgAlaArgAsnAlaArgAspSerGlnValAsnAsn    1560
LeuPheLeuLysSerHisAsnIleValSerIleAlaLeuGlnIleGluSerCysIleArgIleAlaLeuGluSerArgValAlaLeuAlaArgArgAspSerValLeuHisArgProGluLeuGluProValAspLeuAspSerArg    1600
GluArgLeuGlnAspIleValSerAlaLeuGlnGlyPheIleGlyLysGluSerIleLysValLeuThrAlaLeuGluAsnTrpProLeuLeuSerArgAlaArgAsnAlaArgAspSerValLeuHisArgPro    1640
AspAlaArgArgLysCysGluAspAlaLeuArgGlyPheTyrArgGlyLysCysGlnIleSerArgIleLeuGluAspIleLeuSerGlnGluAlaGluGlnAspAlaGlnAlaGluAlaProProGlnAsnThr    1680
MetMetThrArgLysAspProLeuMetAspArgMetAspPheHisSerLysAspArgMetGlnIleLeuGluAspIleLeuSerGlnGluAlaGluGlnAspAlaGlnAlaGluAlaProProGlnGlu    1720
ProProLeuArgGlnLeuGluAspHisLysAspArgGlyTyrTyrGlyAsnIleArgProSerGlyAlaLeuArgGlnIleLeuGluLeuGlnSerLeuThrSerGlnGlnAlaGluAlaProProGln    1760
```

Fig. 2C

```
AsnGlyProLeuSerProGlyGlyProLysProGlyGlyGlyGlyGlyProGlySerSerThrSerArgGlyMetSerLeuAlaGluValGlnCysHisLeuAspLys  1800
GluGlyAlaSerAsnLeuValIleAspLeuIleMetAsnAlaSerSerAspArgValPheHisGluSerIleLeuLeuAlaIleAlaLeuGluGlyLysAsnThrIleGlnHis  1840
SerPheCysArgLeuThrGluAspLysLysSerGluLysPhePheTyrAspArgMetLysValPheAspAlaLysSerAlaThrValAsnThrSerAsp  1880
LeuGlyAsnLysLysLysLysAspAlaSerProSerArgLysLysLysGluLysValAlaArgAspGlnLeuLeuGluAlaSerAla  1920
AlaThrArgLysAlaPheThrThrPheArgArgGluAlaAspProAspAspAspHisTyrGlnSerGlyGluGlyThrGlnAlaThrThrAspProLysAlaLysAspProLeuGluMetSerAla  1960
ValIleThrIleMetGlnProIleLeuArgPheLeuGlnLeuLeuCysGluAsnHisAsnArgAspLeuGlnAsnPheLeuArgCysGlnAsnAsnLysThrAsnTyrAsnLeuValCys  2000
GluThrLeuGlnPheLeuAspCysIleCysGlySerThrThrGlyGlyLeuGlyLeuLeuGlyLeuTyrIleAspLeuLeuLeuGluLysAsnValAlaLeuIleAsnGlnThrLeuGluSerLeuThr  2040
GluTyrCysGlnGlyProCysHisGlyAsnGlnAsnCysIleAlaThrIleGluSerAsnGlyIleLeuAsnAspIleAsnAspIleLeuTyrAsnMetArgProLeuGlyLysLysArg  2080
MetAspLeuValLeuGluLeuLysLysAlaSerAsnAlaSerLysLeuLeuAlaIleMetGluSerArgHisAspSerGluAsnAlaGluArgIleLeuTyrAsnMetArgProLysGluLeu  2120
ValGluValIleLysLysAlaTyrMetGlnGlyGluValGluPheGluAspGlyGluAsnValAlaAspGlyAlaAlaLeuGluPheTyrArgAlaLysHisThrAlaGlnIleGluIleValArgLeu  2160
GlnLeuAlaArgHisAsnLysGluLeuGlnThrMetLeuLysProGlyGlyGlnPheLeuThrLysGlyGluSerLysLeuArgIleTyrTyrThrGluArgAspGluGlnSerLysIleCysAsn  2200
AspArgThrMetGluGlnIleIleValPheLeuProValProSerIleCysGluPheLeuThrLysGlyGluSerLysLeuArgIleTyrTyrThrGluArgAspGluGlnSerSerPhe  2240
AspPhePheLeuArgSerGlyAspPheLeuValMetAsnTrpGlyMetAspSerArgAsnMetSerPheSerSerIleAlaMetLeuIleSerLeu  2280
AsnLeuAlaValLeuMetAsnLeuLeuValAlaAlaPheTyrProHisTrpSerGlyLeuLeuProThrLeuProGlyLeuGlyAlaPheAsn  2320
AlaIleValIleAlaLeuProLysProIleSerGlyIleGluArgAlaLeuIleAlaSerThrIleLeuPheThrArgGlyTyrArgPheLeuLysIleGlyAspValGlyLeuAspTyrHisLeuLeuIle  2360
ValCysAsnLysIleIlePheLeuMetSerPheValGlyAsnCysGlyThrPheTyrLeuLeuLeuPheAspLeuValAsnValIleLysSerValThrArgAsnGlyArgSerIle  2400
CysAlaMetGlyLeuPheValHisGlyPhePheTyrSerLeuLeuLeuPheAspLeuValAspLeuValAsnValAspSerValThrArgAsnGlyArgSerIle  2440
IleLeuThrAlaValLeuAlaLeuIleLeuValGlyPheSerIleValGlyIleTyrLeuPheLysGluAspLysPheLysGlyIleArgPheAsnGlyAsnLeuValThrAlaValPro  2480
GlyThrGlyGluSerLeuAlaAsnAspPheLeuTyrSerAspValCysArgValGluThrGlyGlyIleGluAsnCysSerGlyThrLeuProAlaGluLeuProLysGluThrGlu  2520
GlnAspLysGluHisThrCysGluThrLeuLeuMetCysIleValThrValLeuSerIleIleIleIleIleValAlaLeuAsnLeuIlePheGlyValIleIleAspThrPheAlaAspLeuArgSerGluArgSerGluLysGluPro  2560
LeuPheAlaAlaArgValIleTyrAspLeuLeuPhePheMetValIleIleIleIleValLeuLeuAsnLeuIlePheGlyValIleIleAspThrPheAlaAspLeuArgSerGluArgSerGluLysGluProLysGln  2600
LysLysGluGluValIleLeuLysTyrThrCysPheIleCysGlyLeuAsnArgAspLysPheAspAsnLysThrValThrPheGluGluHisIleLysGluGluGluHisIleLysSerAsnMetTrpHisTyr  2640
LeuCysPheIleValLeuValLysValLysAspSerTyrThrGlyTyrProGluSerTyrValAlaGluMetIleArgGluArgAsnLeuAspTrpPheLeuArgMetArgAlaMet  2680
SerLeuValSerSerAspSerGluGlyGluGlnAsnGluLeuArgAsnLeuGlnGluLysLeuGluSerThrMetLysLeuValThrAsnLeuSerGlyGlnLeuSerGluLeuLysAspIleGluLysLys  2720
GlnMetThrGluGlnArgLysGlnLeuGlnArgIleLeuGlyLeuGlyHisProProHisMetAsnValAsnProGlnProAla  2749
```

Fig. 3A

```
GCTGAAGCGTTTCCTCAAGCCTGCCGGGTGGGAGGAGGAGGTGGTGGTGGAGGAGAGGAGGAGGTGGAGGCCAGAGGTGGAGAGAGAGAAAGCCACGCCCAGAGGAGGTGTGGGTGTT      120
CCGTCCCATCCTAACGGAACGAGCTCCCTCTTCCCGGACATGGGATTGCCCAGCGGCTGCTAACCCCTCTCCTGGTCCTGATCCCCAAACCCGGCTGGCTCCCGGTCACCAAGGAGC      240
TGATTACAAGGGACCAGGATTGCATCCTGGGCGTCCATTGGCTGCTGCCTAGAGAGTGCCACCTTAGGCTCTGGTCAGGCTTTCAACACGGACATGTCTGACAAAATGCCAGTTCCTACATAT      360
TGGAGACATTTGTTCTCTGTATGCGGAGGGATCTACGAATGGATTTATCAGCGACCTTAGGCTTGGTTGATGACCGTTGTTGTTGTACAGCCAGAAGCCGGGGACCTTAACAATCCACCCAA      480
GAAATTCAGAGACTGCCTCTTTAAGCTATGTCCTATGAATGATCATCCGGCACAGAAACAGTTCTGGAAAGCTGCTAAGCCCGGGGCCAACAGCCACTACAGATGCAGTGCTGCTCAACAA      600
ATTGCATCATGCTCAGACTTGGAAAAGAAGCAGAATGAGACAGAAAACAGGAGAAATTGTTGGGGACCGTCATCCAATATGCAAGGTGATCCAGCTCCTGCATTTGAAAAGCAATAAATA      720
CCTGACTGTGAATAAGAGGCTCCCAGCCTTGCTAGAGAAGAATGAGGGTGACGTTGGACGAGGCTGAGGTCCTGGTTTACATTCAACCATTTTACAAGCTTCGCTC      840
CATCGGAGAGACAGTGGTCATAGGCGACAAGGTAGTTTTCATGAAATGGATGATAACAAAGACGACATTCTCAAAGGAGGTGATGTGGTGAGCCTCTTCCATGCCGAGCAGCAAGAGAAGTTTCT      960
CGTCAACTGTAATACAAGCTGGAAGATAGTGCTTTTCATGACCATGTGTTCCTGAGGACGCAGCAGTCAGCCACCGGCAGCAGTCACCCACGTCGGCCACACCTCAAAGCCCTGTGGAAGTAGTCGAGCAGGACCC      1080
ATGTCGGGTGGAGCTGGGTACTGGAATAGCCTCTCTTCCGGTTGAAGAATAGGTTGAGAAGGCAAGGTAGACCCTGCCTGAAGGCAACGACATCTCCTCCATCTTTGAGCTAGA      1200
CTCAGTGGACCCTGATCAGGATGCATCTCGAGTAGGTTGACACGCCTTGTCTCCCCTGAAGGAGTGAAGGAACACCATCGAGAGCGGGCAGAAGCTGATGAGGAACGAAGCTGATGAGGAACGAAGCTGTGTCACGAGAATGATCGCCGCAA      1320
CCCACGACTCTGGGTGGAGGTGAAAATTGGTACCTCTCCCCTGAAGGAGGAGCACCATCGAGAGCGGGCAGAAGCTGATGAGGGAACAGAAGCTGATGAGGAACATATTGCCGACTCTGCTACAGGGTCCTGCCGACACTCACAGGAAGAACCA      1440
GAAGCCTGTGTGATGCTGAAATTGGTACCTCTCCCCTGAAGGAGGAGCACCATCGAGAGCGGGCAGAAGCTGATGAGGGAACAGAATATTCTCAAGCAGATCTTCAAGCTGTTCACGGTGAACTAACTCTGG      1560
GGTGCTGGGCTCCATCGGCTTGAAGTTGTCTTCTCTAAGCCCAATCGAGAGCGGGCAGCCCATGCTGGCTCATGACGGAGCCCAGGTTCTTGGATTACCTCTGACCTGTGCGCATCCCATGAACAAGTCAATCCCTGTGACACAGGAGCT      1680
CCAAGAGCTGCTTGAAGTTGTCTTCTCTAAGCCCAATCGAGAGCGGGCAGCCCATGCTGGCTCATGACGGAGCCCAGGTTCTTGGATTACCTCTGACCTGTGCGCATCCCATGAACAAGTCAATCCCTGTGACACAGGAGCT      1800
GGATGCCCGATGCTTCGGCTGGAGGAGCTGGGGATCAGCGGGATCAGAGAAGCAGATTGGCTCATGCAGAAGAGGCCCAGGTTCTTGGATTACCTCTGACCTGTGCGCATCCCATGAACAAGTCAATCCCTGTGACACAGGAGCT      1920
GGAGTACATAGCCAAGCAGATTGACACGTTTGGCTTCAGCCTGGTGCGAAAGAACAGGAGCCCAGGTTCTTGGATTACCTCTGACCTGTGCGCATCCCATGAACAAGTCAATCCCTGTGACACAGGAGCT      2040
CCCGGCAGAGATTGACACGTTTGGCTTCAGCCTGGTGCGAAAGAACAGGAGCCCAGGTTCTTGGATTACCTCTGACCTGTGCGCATCCCATGAACAAGTCAATCCCTGTGACACAGGAGCT      2160
CATCGTAAAGCTGTGCTCAATCCCACCAATGCTGCTCATTGAGACAAAGAGATCGTGCATCGCTGAGGACAGCAACAAGAAGACTCGTAGTAACGTACCTGGCCATGCTGGACACCTGATGTTGATCTCATTCTCCGCTGTGCATTGCGA      2280
GGATGAGGAGAGGTGTGGCTGTCTTGGAGGACAGCAACAAGAAGACTCGTGCTGAGAGCGAGCCGCACCTGCCAAGAGCAGTGACACCTGATGTTGATCTCATTCTCCGCTGTGCATTGCGA      2400
CTACTACAGATATCAGCTGAACTGAACGCAGCTCTGCGAACATGCTCTCGACCCCAGTACCTGCGACCGAATGCGACATCAGCAAGCGTAGTAACGTACCTGGCCATGCTGGACACCTGATGTTGATCTCATTCTCCGCTGTGCATTGCGA      2520
GAACCTCCCTACGACCTCCAGGGCATCTTTGCAAGGACATGTCTCGAAGGATGCCGTCCATCCCCATTCGACCTCCAGGATGAAATGCGACATCAGCAAGCGTAGTAACGTACCTGGCCATGCTGGACACCTGATGTTGATCTCATTCTCCGCTGTGCATTGCGA      2640
CTCTGAGATCCCCATTGATGACTGTGTCCATGTGACCAGTATTCCCCATTAGCACGAGCAGGATGAAATGCCAGAATCTCATATACTTGGTTTCTAGCGTATTAACGAGAGATAAGCCAGCAGTGACAGTCACCTTCCAGAGGACAGTCAAGAGATCATAACCAAGATCCT      2760
ATTCCCTTCTCTGTAAGGAGAAAATAAGCTCACGTTTGAGCTTGTGACTTAGCCAAGATGACAAGATGAACTAGCCACAGGAATAAAGGCAGCAGTGCAGATCAAGATAATAAGGAGAATAAGGACACAGCAGTCACCTTCCAGAGGACAGTCAAGAGATCATAACCAAGATCCT      2880
CTTGGCAATCTTAGACTGTGTGCATGTGACCACTATCTCCCATTAGCACGAGATGACAAGATGAACTAGCCACAGGAATAAAGGCAGCAGTGCAGATCAAGATAATAAGGAGAATAAGGACACAGCAGTCACCTTCCAGAGGACAGTCAAGAGATCATAACCAAGATCCT      3000
GACCCAGGTGTGCTGCCGGGGAGGAGGCTTCTTGCCCATGACTCTTGCCCATGACTCTTGCCCATGACTCTTGCCCATGACTCTTGCCCATGACTCTTGCCCATGACTCTTGCCCCCAAGATCCTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGACTCTTGCCCATGAC      3240
```

Fig. 3B

```
GTTGAAGATCATTGAAATACTCCAGTTTATTTTGAATGTGAGATTGGATTATAGGATCTCCTGCCTCCTCTGTATATTTAAGCCGAGAGTTTGATGAAAGCAATTCCAGTCATCAGAAAC      3360
ATCCTCCGGAAACACCAGCCAGGAAGGCCAAGTAATGCCAGGTCGTTGCTTCACTTTGAACACATTGAAGAACAAGCGAAGGCATCTTTGGAGGAAGTGAGGAGAACACACCTTTGGA      3480
CCTGGATGACCATGGTGGCAGAACCTTCCTCAGGTCGTCGTCCACTTGACAATGCATTACCCACCCTGGTCTGTCGGGGCCTCGCAGCTCCCTTCCGCACTTCAGCCAGGCCA      3600
GGAGGTCCTTCAGGGCCTTCAAACAGGTTCAACTGCTGGTTACTAGCCAAGGAGCCTCCCCATGGACGGAGCCTCCGGTGAAAATGAGCATAAGAAAACCGAGGAGGGACGAACAAGCCACTCAAGCACGAGAGCACCAGCAGCTA      3720
CTCGGGTGTACAAAGGCCAAGGTCTCCCATGACCCATAGCAAGCTCTCGGTGACGGAGGCCCTCCGTGAAAATGAGCATAAGAAAACCGAGGAGGGACGAACAAGCCACTCAAGCACGAGAGCACCAGCAGCTA      3840
CAACTACCGAGTGGTGAAGAGATTTTGATTCGACTTAGCAAGCTCTCGGTGACGGAGAGCCCTGAGGAGGAGCGCTCGGTGAGGAGAGCGGAAGCAGCAGCAAGACGTGCTGAGGAACATGGGCCACA      3960
CCCTGTGGTGGTGGAGCTGCTGCAGATCCCCTACGAGAAGGCCGAAGACACAAGATGCAAGATCATCGGGCTGCCTCATGAGTTTGCAGAATTTCTGCAGGCAACCAGCAGAA      4080
TCAAGCTTTGCTGCATAAACACATAAAACCTGTTTCTCAAGCCAGGATCCTGGAGGCAGTGACGATGCAGCACATCTTCATGAACAACTTCCAGCTGTGCAGTGAGATCAACCAGAGAGT      4200
GGTCCAGCAGTTTGTTCACTGCATAGAGACCCACGGTCGAAACGTCGAAGACATTCTCCAGACGATTGTCAAGGCAGAAGGGAAATTCATTAAAAAGTGCCAAGACATGGTCAT      4320
GGCTAGCCTTGTCAACTCTGGAGGAGGACGTCCTCGTTGTCTACAATGACAGAGCCTCTTTCCAGACACTCTGATCCAGACTGATGCGGTGACCGGATGGATGGATGAGAACAGCCCTCT      4440
CATGTACCACACATCCATCTGGTGGACCCGTCTTGCCCGTGCACAGAGGCCAAGAATGTCAACTCAACTCCAAGTCCAACTCCTTGCTCCCTCGATGACATCGTTCGTGTCACTCA      4560
TGAAGACTGGCATGCCCGGAGGTTAAGAATGCCTTACATTAACTTCCTGAATCACTCTCTATGTGGATACGGAGACTCCATTCTGGAGAAGTAGCTCACTGAAATCGTGATGAGCATCGTACCACCTTCTTCAG      4680
GAATTTCCTGCTGGACATCGCAGGGCCTGTAACACACACCGGACAGGAAGCACGGCAGACTCCATTCTGGAGAAGTAGCTCACTGAAATCGTGATGAGCATCGTACCACCTTCTTCAG      4800
CTCTCCCTTCTCAGACCTCTGTAAGCTCTGCACCTCTGCTGACCCTGACCGCCAGCCTGTCTTTGTGACCGTGTTCCAAGGCGTGTTCCGGAGACAGCCAAGTCAACACCTTCCTGAAGTCCCACAACATTGTCAGAA      4920
GGTGAGAGCCTGAACTGGCGTTATCAGCCCGAAACGCCTCCCAGAGACGCCCGGAACGCCTCCCAGAGACCTGTACTGCACAGAGACGCATCCAGAGAACTCATTGAGAGGTTACAGGACATCGTCTGCCCTAGA      5040
AACAGCCCTGAACTGCCGGGTTATCAGCCCGAAACGCCTCCCAGAGACGCCCGGAACGCCTCCCAGAGACCTGTACTGCACAGAGACGCATCCAGAGAACTCATTGAGAGGTTACAGGACATCGTCTGCCCTAGA      5160
GGACCGGCTCAGGGCCTGGTGCAGGCTGACGTGTCTGTCGTCGTGGAGGAGAATGAAGAGAAACTATGCCATTCATTAAAGTCTTACGACCCCTCAGGGAACCTCAGGGAATGATGACCAAAGACACAGGAGGCTATGGAGAGAA      5280
CATCTCCAGCTAATAAAACATACCCAAGCCAACTGCTGGAGGAGAATGAAGAGAAACTATGCCATTCATTAAAGTCTTACGACCCCTCAGGGAACCTCAGGGAATGATGACCAAAGACACAGGAGGCTATGGAGAGAA      5400
GCAAATTTCCATTGATGAATCGGAAAATGCCAGCTCCCACAGGCACCCGAAGCTGAGAACTCCACAGAGCAGGAGCCTTGAACCAAGTCCACCCCTGAGGCAACTGAGGCAACTGGAAGACCATAAAAG      5520
GGGTGAGGCACTCCGACAAATTTGGTCAACCGTTACTATGGAAAACATCAGACCTTCAGGAAGAAGAGAGCCTTACCAGCTTTGCAATGGCCCACTATCACCAGGAGGACCAGCAA      5640
GCCTGGTGGAGGAGGGAGTGCTTGGAGATCTAGTTGAAAGCCATTCCATCGAAAGCCAGGGTGAGATGAGCCTGGCTGAGTCAGTGCACCGCCAAGACCCATCCAGCCACTGCTGGATCTCAT      5760
AATGATGCAGAGAAGTCCCAGTGACCGAGTATTCCATGAAAGCCATTCCATCGAAAGCCAGGGTGAGATGAGCCTGGCTGAGTCAGTGCACCGCCAAGACCCATCCAGCCACTGCTGACAGAAGATAAGAA      5880
ATCAGAGAAGTGCCCGTCTCGGAAGAAGCCAAGCATTACCAGTCTGGGGAGGCACCCCAGACATCTCCAGAATTTCCTTCGTTGCCAAAATAATAAGACCAACTACAATTTGGTGTGTGAGACACTGCAGTTTCTGACTGTATTTGCG      6000
CAGGGATGCCGCCGTCTCGGAAGAAGCCAAGCATTACCAGTCTGGGGAGGCACCCCAGACATCTCCAGAATTTCCTTCGTTGCCAAAATAATAAGACCAACTACAATTTGGTGTGTGAGACACTGCAGTTTCTGACTGTATTTGCG      6120
GGAGGGCCGACCCTGATGACCTCGAAAACCAACCGAGATCTGCCAGAATTTCCTTCGTTGCCAAAATAATAAGACCAACTACAATTTGGTGTGTGAGACACTGCAGTTTCTGACTGTATTTGCG      6240
CCTGCAGCTGCTGTGTGAAAACCGGAGGCCTTGCTCTTCTTGGACTGTACATAAATGAAAAGAATGTAGCACTTATCAACCAAGAATGCCAATCCTGTGCAGACACTGCAGTTTCTGACTGTATTTGCG      6360
GAGCAGCACCGGAGGCCTTGCTCTTCTTGGACTGTACATAAATGAAAAGAATGTAGCACTTATCAACCAAGAATGCCTGAAGGGCTTCAAGGTGCACGAGTACTGCAAGGGCTTGCAATGCACGAGAACCA      6480
GAACTGCATGGCCAGCCACGAGTCCAGTGCAGGGGAATGGATGCACGAGAACAACAGGAAAGGGAAAGAATCCCTCGGGAAAGAACGGGATGGAAAAGAACGGATGGAAAAGAACGAATGC      6600
```

Fig. 3C

```
TTCGAAGCTGCTACTGGCCATCATGAAAACAGAGACACGATAGTGAAAAATGCAGAGAGGATCCTGTACACAATGAGGCCCAAGGAGCTGGTGAAGTGATCAAGAAGGCCTACATGCAAGG    6720
TGAAGTGGAATTTGAGGATGGGGAGGAACGGTGAGGATGGAGCTGCCTCACCCAGGAACGTGGGCCACAACATCTACATCCTCGCTCACCAGTTGGCTGGGCATAACAAAGAACTTCAAAC    6840
CATGCTGAAACCTGGAGGCCAGGTGGATGGGGATGAAGCTCTGGAGTTCTACGGAAGCACACAGCCACAAATTGAGATTGTCAGACTGGACCGGACAATGGAACAGATCGTCTTCCCTGT    6960
GCCCAGCAGCATCTGTGAATTCCTGACTAAGGAATCCAAAACTTCGAGAAGATCCAGCCCTGTCTTCTGTCCCGAAACATGTCTTTCTGGAGCCAGCATCTCCTTCAACCTGGCCGTCTCCAACGCTGCTGGTGGC    7080
CGAGATGAACTGGCAAGGAAGAAACTTCGAGCCCAGCCTGCTGCTCCTGAACACTGGTCAGGCCTCGGGCCTCCATGCAGGCCATGCTCAGGACAGCCATCCATCTCTCGGCCATTGTCATTGTCATTGTCATGCTCTGCCCAAGCCCACGG    7200
GTTTTCTATCATCCATTTAAAGGAGTGAGGGGAGGAACACTAGAGCCACACTGGTCAGGCCTCCCATCCCCATGTCCAATAAATCATCTTCCTGATGAGCTT    7320
CATCCGGGCCTTAATTGCTTCTACAATCCTACCACTGATATTTCAGTTGGGTTGCAGCCGACAGCTGATTTCTCGCTGGAGTTCCTGTATGCACTACTCATTGTCCATGCCTCTTCGTACATGAGTTCTT    7440
TGTGGGCAACCTGTGGGACCTTCACCAGAGGCTACCGGCGCCATGGTTCTGGATGTGGAGTTCATTCAGTTCATTAAAGTGTCACCGCCAATGACGGTCCATCATCTTGACAGCGGTCCTGGCTGTCTGATCCTGGT    7560
CTATAGCTTGCTGCTTTTGATTTGTGCTATCGTGTCTTCAAGGATGCTATCGTCTTCAAGGATGACTTTATCTTGCAGAAGTAGATAGTTGCCCAATGAAAACAGTGTTCCAGAAACTGGCGAGAGTTGGCCAACGATTTCCT    7680
TTAACCTGTTCTCAATTGTGGCTATCGTGTTCTTCAAGGACGGGGAGAACTGCACCTCTGCACCCAAAGAAGAGAGCTGCTGCTCAAGCTCCGGGCTCATCATCCGACACCCTGTTTGCTGCAAGGTGATCTACGACCTCCT    7800
GTACTCTGATGTGTGCAGGTAGAGACGGGGAGAACTGCACCTCTGCACCCAAAGAAGAGAGCTGCTGCTCAAGCTCCGGGCTCATCATCCGACACCCTGTTTGCTGCAAGGTGATCTACGACCTCCT    7920
CATGCATCGTCACTGTTCTGAGTCAGCTGCTGGGAGGCTGCGGAGTGGGGAGTGGAGGTTCGCCTGCTCATCGAGCTGGAGCCTCTGCTCAAGGTGCTGCACCATCCCAAAGAAGGAGCAAAGAAGGAGGAGATCTTAAAAACCACCTTCCT    8040
CTTCTTCATGCATCGTCATCATCCTGCAACCTGATTTGACTGTACTGTCATCAACGAAGAACACATGGCCACTATCGTGCTTCATCGTGTCTGGTGAAGTGAAGA    8160
CATCTGGGCTTGGAAAGGGACAAGTTTGACAATAAGACTGTCACCTTTGAACAATGAGCCGAAAGAAAACCTTGATTGGTTCCTCAGCTGTCAGAAGTAAAGGACCAGATGACAGAACAGAGGAAGCAGAACAAAG    8280
CTCCACAGAGTACACCGGGCCTGAGAGTTACGTGCAGGGAGAAGCTGGAGTCTACCATGAAGCTGTCAACCAGGCAGCCGGGCTCTAGGGAAATGAGGCAGAGGCAGAGCTGTCCAGCCCTCGTATATCACTGTCAGGGTGGGTACGGCT    8400
GAACGAGCTGAGGAACCTGCAGGAAGACTGGAGTCTACCATGAAGCTGTCAACCAGGCAGCCGGGCTCTAGGGAAATGAGGCAGAGGCAGAGCTGTCCAGCCCTCGTATATCACTGTCAGGGTGGGTACGGCT    8520
AATCGGCCTTCAGGACATCGTCCTACAATGAATGTCAACATGATGTGCGCTTAGTACCGGTACACTCCCAAAAATATTAAAAATGCCTTTTGGAAGGACTACAGAGAAAGTACCTGATTTGCACTTGAACCAGATTATAGATTTAAAAGTATATG    8640
CATGGTTCTGATTCCCACTCAAGGTGATCTGTTCACTCTGCCAAAAATATTAAAAATGCCTTTTGGAAGGACTACAGAGAAAGTACCTGATTTGCACTTGAACCAGATTATAGATTTAAAAGTATATG    8760
AGCTCTGTTGGCATGGTGACTTGCACTTGTCACTCTGCCAAAAATATTAAAAATGCCTTTTGGAAGGACTACAGAGAAAGTACCTGATTTGCACTTGAACCAGATTATAGATTTAAAAGTATATG    8880
ACATGTATTTGTATTAAAACTAGAATAGCCAGTATTGTTAAATATCAAAATGGTTAAAATATCAAAATGCTGCTGTCGTGCCAATAACAAATATAGCGAGTTTCGCCCCGTGGCAATTTGTACCTTGTAA    9000
TCTTTGAAGCTGATTTGTTGATACTCGTGTAATAATGGTTAAAATATCAAAATGCTGCTGTCGTGCCAATAACAAATATAGCGAGTTTCGCCCCGTGGCAATTTGTACCTTGTAA    9120
TTATCCTATGGTGATGCGTGTTTCTGCGTTTCGTTGCATTAGTGCCCCTGTATCCTAGTGATAACTGGATATCCAGGTCTGTGAACCATTCAAACAGCATCATTTTGAGAAAAGCAACTTAGTT    9240
TCAAGGATAATTTTCAAGCTTCAAAATTCATTTAAGATGTTCTTTAAGAGACATGTAGAGGCTCACACTTTAGTGAAGGAGTGAATTAATTTTAAGGAACTTT    9360
TTACATGACGTTTGGAATAACAGCATATTGCTGACCAGTCAGTGCATCTCCCGGTGAATTTTGATGTCACGTTATGCAAATGAGTTAGTGATGTTTCTAGATTTTCTTCCTCTG    9480
AACCAATGCAGTAGGTAAGAAGTTATTATGCGTATTGCTACTCATATACATTCACATGATTCTTTGTCACATGATTTCTTTCTTCTTCTCCGATGGTATCACAGAGGAGCTGCCCTAGGGTACGTAGCTGAACAC    9600
TGACAATGCCGTTCTCTCTGAAAGCACCACGTTTGGGTTTTATTTCTCCACAAAGTTTAAAAACTTTAAAAACTGAACCGTATGCAACGTTCGAACCAAGTCAAGTTTGTAAATGCATACCTAAAAATATTTAATAAACGATGC    9720
ACCTGGGTCTCGCTTTACTAGAACCGTCTCGCACAAAGTTTAAAAACTGAACCGTATGCAACGTTCGAACCAAGTCAAGTTTGTAAATGCATACCTAAAAATATTTAATAAACGATGC    9840
AGAATCCTAAAAAAAAAAAAAAAAAAAAAA                                                                                                    9871
```

DNA CODING AN INOSITOL 1,4,5,-TRIPHOSPHATE BINDING PROTEIN

This application is a continuation of Ser. No. 08/228,004 filed Apr. 15, 1994, which is a continuation of Ser. No. 08/087,468, filed Jul. 8, 1993, which is a continuation of Ser. No. 07/793,277 filed Nov. 12, 1991 which is a division of Ser. No. 07/550,554 filed Jul. 10, 1990, all abandoned.

FIELD OF THE INVENTION

This invention relates to a polypeptide capable of binding to inositol 1,4,5-trisphosphate (hereinafter referred to as "IP3"), a deoxyribonucleic acid (hereinafter referred to as "DNA") coding for said polypeptide, a recombinant, plasmid with said DNA or a part thereof inserted therein, a microorganism and animal cells each harboring said plasmid, and a method of producing said polypeptide. IP3 is one of the most important intracellular mediators involved in the intracellular mediator mechanisms and serving to adjust the calcium concentration in the cell. The polypeptide according to the invention binds to this IP3 and thereby functions like a receptor for causing various reactions. The polypeptide and DNA coding therefor according to the invention as such are expected to be useful as drugs, for examples as cardiotonics, or diagnostic reagents. They are also usable widely in developing drugs, for example in screening out and evaluating such drugs as calcium antagonists of a novel type.

BACKGROUND OF THE INVENTION

Supattapone et al. reported that a polypeptide having IP3 binding activity was purified from the rat cerebellum [Surachai Supattapone et al, Journal of Biological Chemistry, 263, 1530 (1988)]. The amino acid sequence of this polypeptide is not specified, however. Nordquist et al. cloned randomly three clones of complementary DNA (hereinafter referred to as "cDNA") specific to the mouse cerebellum [Daniel T. Nordquist et al., The Journal of Neuroscience, 8, 4780 (1988)]. Although one of them has a high level of homology to a DNA fragment according to the invention, no mention has been made of the polypeptide encoded by this cDNA having the ability to bind to IP3. This cDNA constitutes only a part of the DNA according to the invention. Maeda et al. purified a glycoprotein, P400, occurring specifically in mouse cerebellum Purkinje cells and having a molecular weight of 250 kilodaltons (Kd). They failed, however, to show that the protein was able to bind to IP3 [N. Maeda et al., Journal of Neurochemistry, 51, 1724 (1988)]. Previously, neither production, by means of recombinant DNA techniques, of a polypeptide capable of binding to IP3 nor determination of the primary sequence of such polypeptide or a gene coding therefor through analysis of such a gene has been reported.

SUMMARY OF THE INVENTION

Accordingly, it is an object of the invention to provide, in large quantities, a polypeptide capable of binding to IP3 and cells allowing the expression of such polypeptide, since such polypeptide and/or cells can be expected to be useful as a drug and/or diagnostic reagent and, furthermore, are possibly suitable in the screening and evaluation of novel drugs.

The present inventors succeeded in cloning, in *Escherichia coli,* a mouse cerebellum-derived cDNA coding for a polypeptide capable of binding to IP3 and in determining the entire base sequence of the cDNA. Thus they could determine the amino acid sequence of the polypeptide. They also constructed cells allowing high-level expression of this polypeptide. Further, they found a region in which a cDNA coding for a polypeptide capable of binding to IP3 derived from other animal species can be readily cloned. These successes have now led to completion of the present invention.

Thus this invention provides a polypeptide capable of binding to IP3, a DNA coding for said polypeptide, a recombinant plasmid containing said DNA as an insert, a microorganism or animal cell line harboring said plasmid, and a method of producing said polypeptide using said microorganism or animal cell line.

BRIEF DESCRIPTION OF THE DRAWING

FIGS. 2(*a*), 2(*b*) and 2(*c*) combined are the amino acid sequence of the IP3-binding polypeptide of the invention;

FIGS. 3(*a*), 3(*b*) and 3(*c*) combined are the DNA sequence coding for the peptide of FIG. 2.

DETAILED DESCRIPTION OF THE INVENTION

The IP3-binding polypeptide according to the invention specifically has the amino acid sequence shown below in FIGS. 2(*a*), 2(*b*) and 2(*c*) or has at least 80%, desirably at least 85% and preferably at least 90% homology to amimo acid sequence of FIGS. 2(*a*), 2(*b*) and 2(*c*).

While the DNA according to the invention may be any of the DNAs coding for the polypeptide specified by the amino acid sequence shown in FIGS. 2(*a*), 2(*b*) and 2(*c*), the DNA specified by the nucleotide sequence shown below in FIGS. 3(*a*), 3(*b*) and 3(*c*) is a preferred example.

Figure 2A:
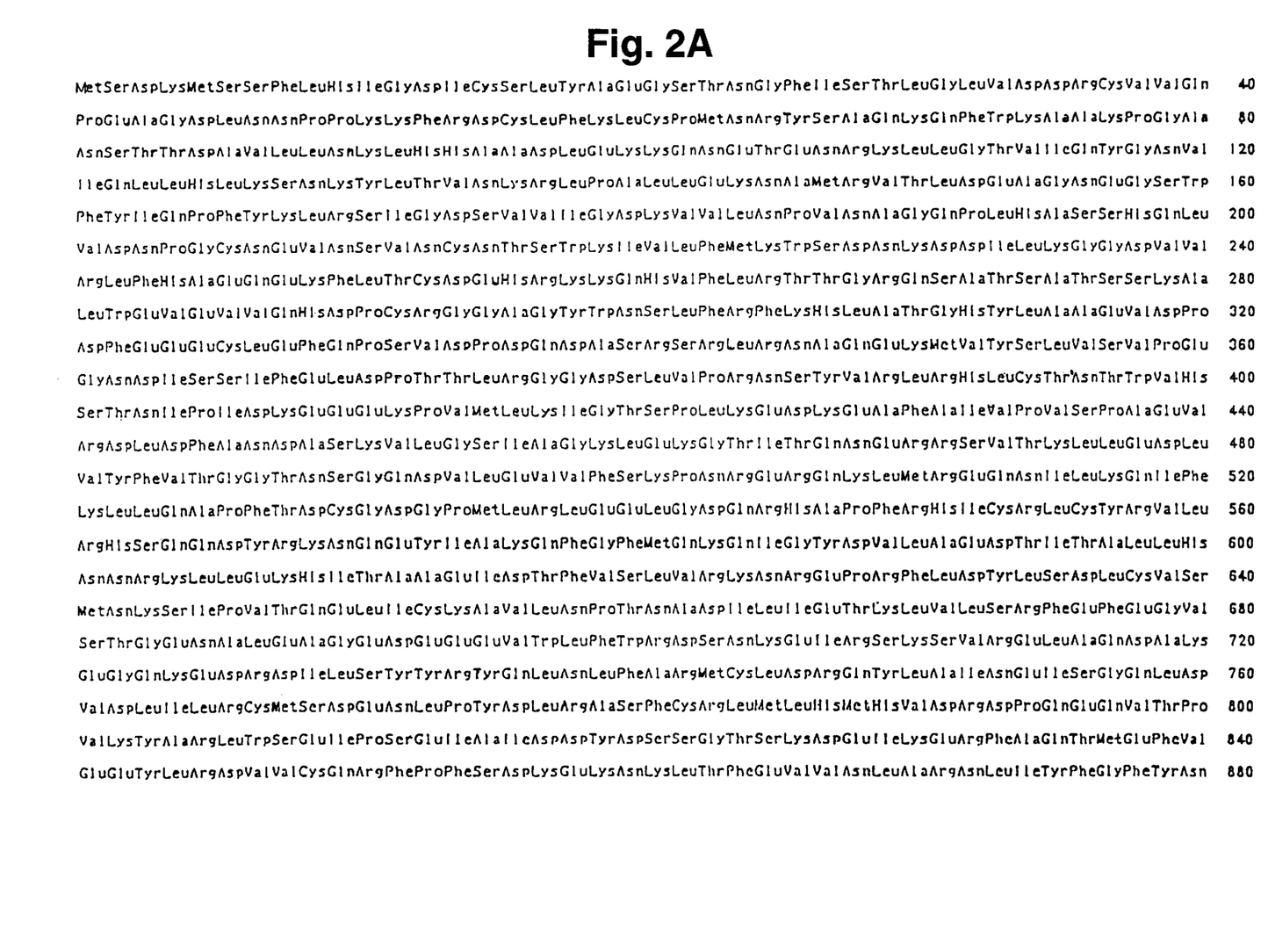
Figure 2B:
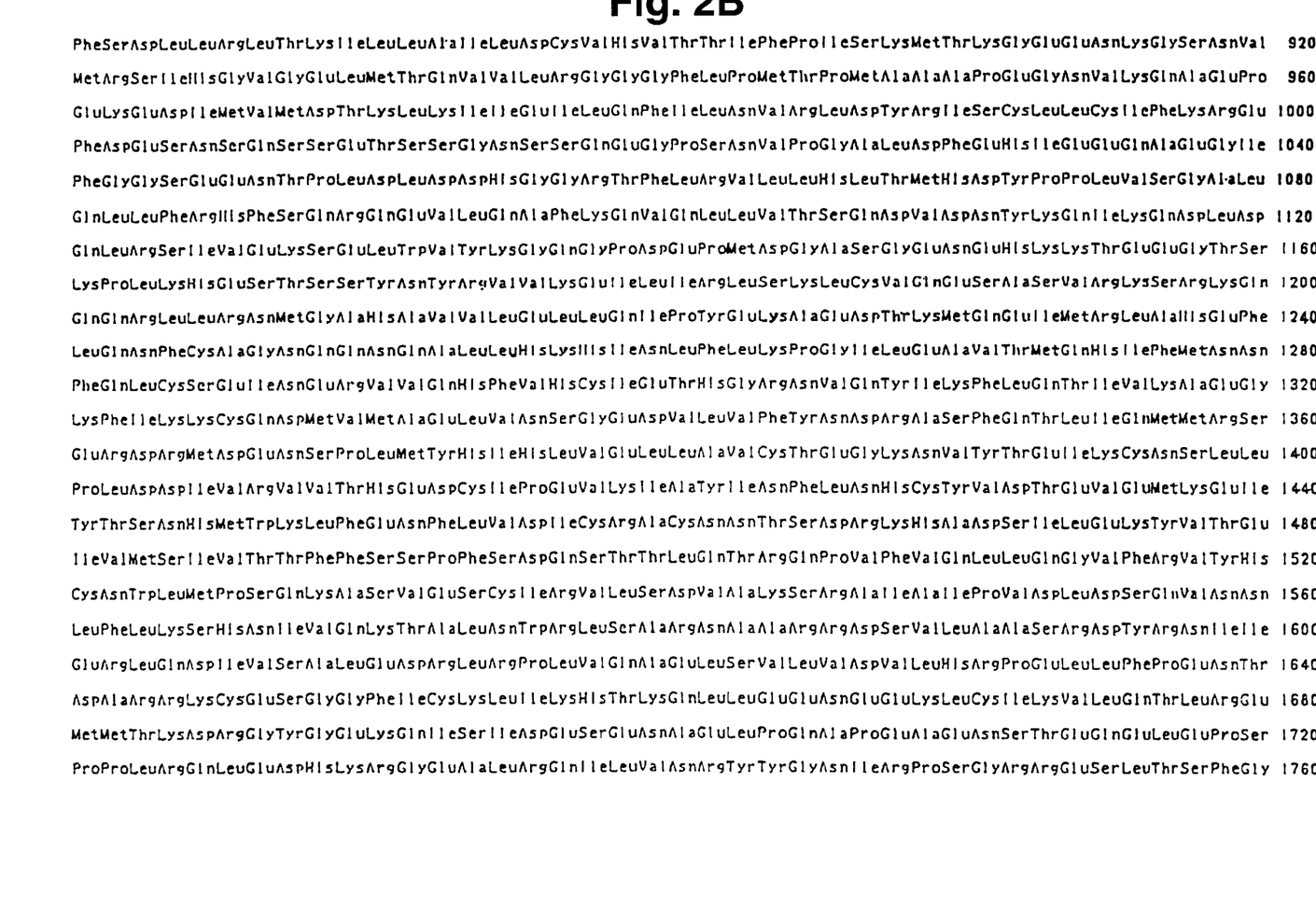
Figure 2C:
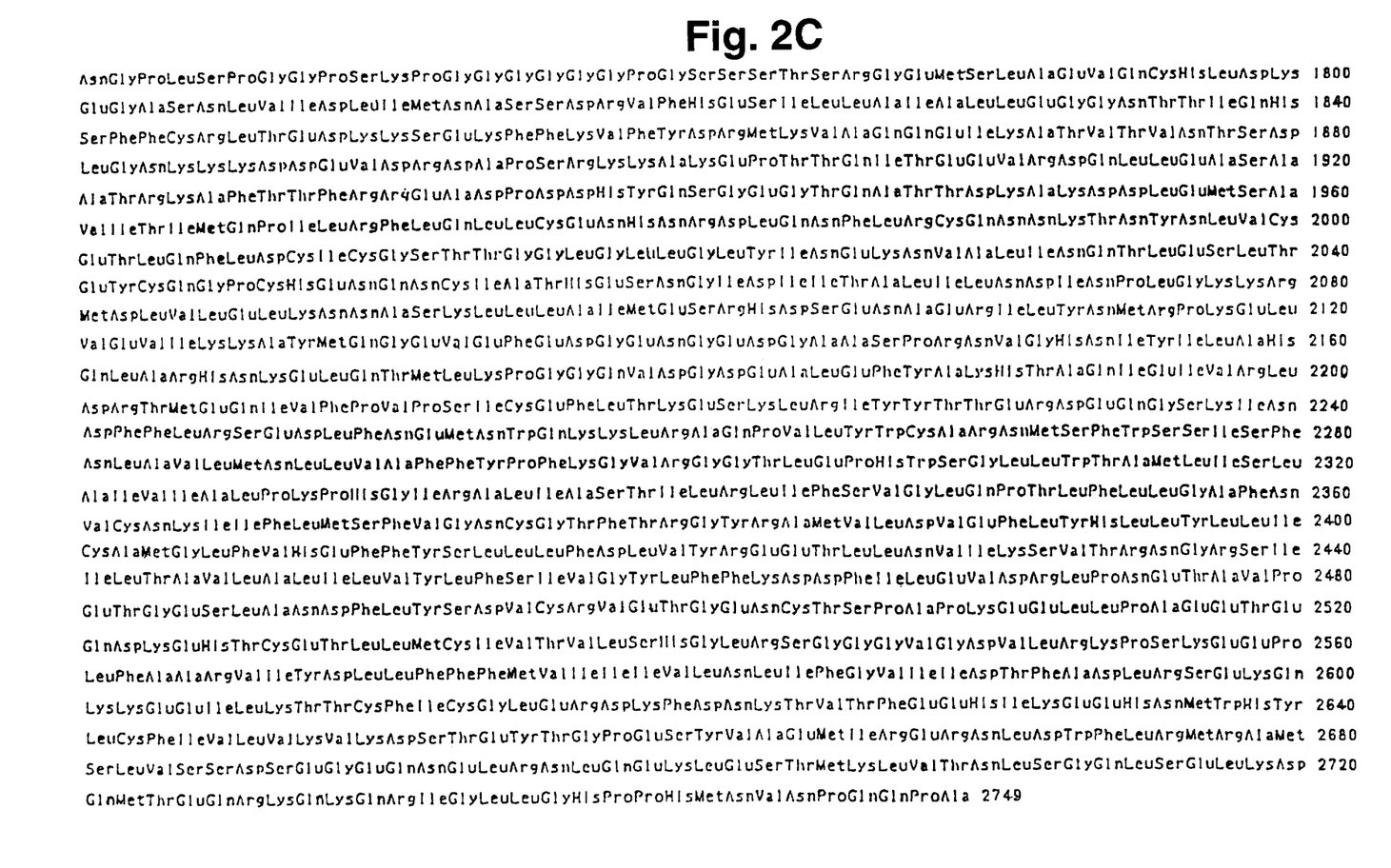
Figure 3A:
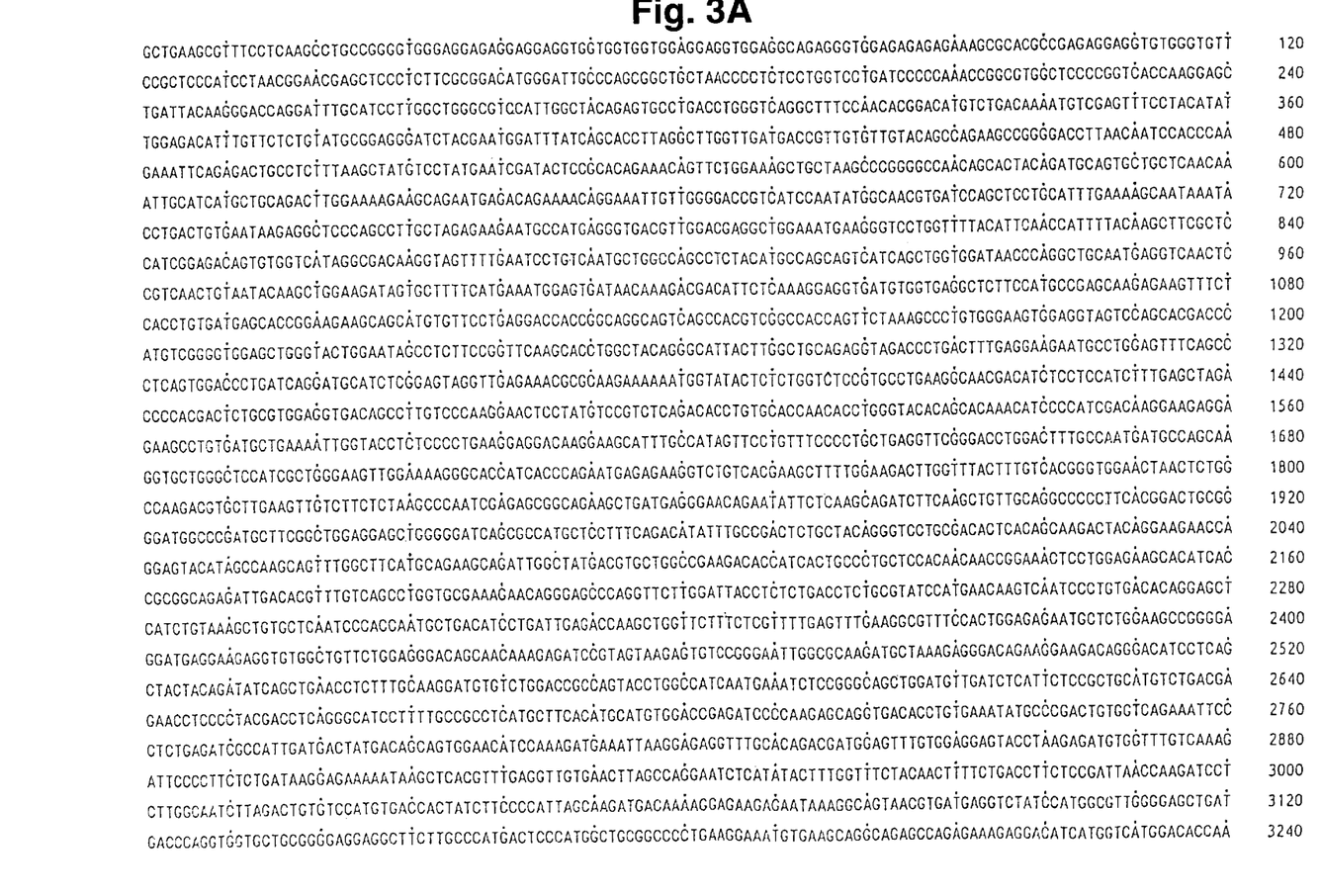
Figure 3B:
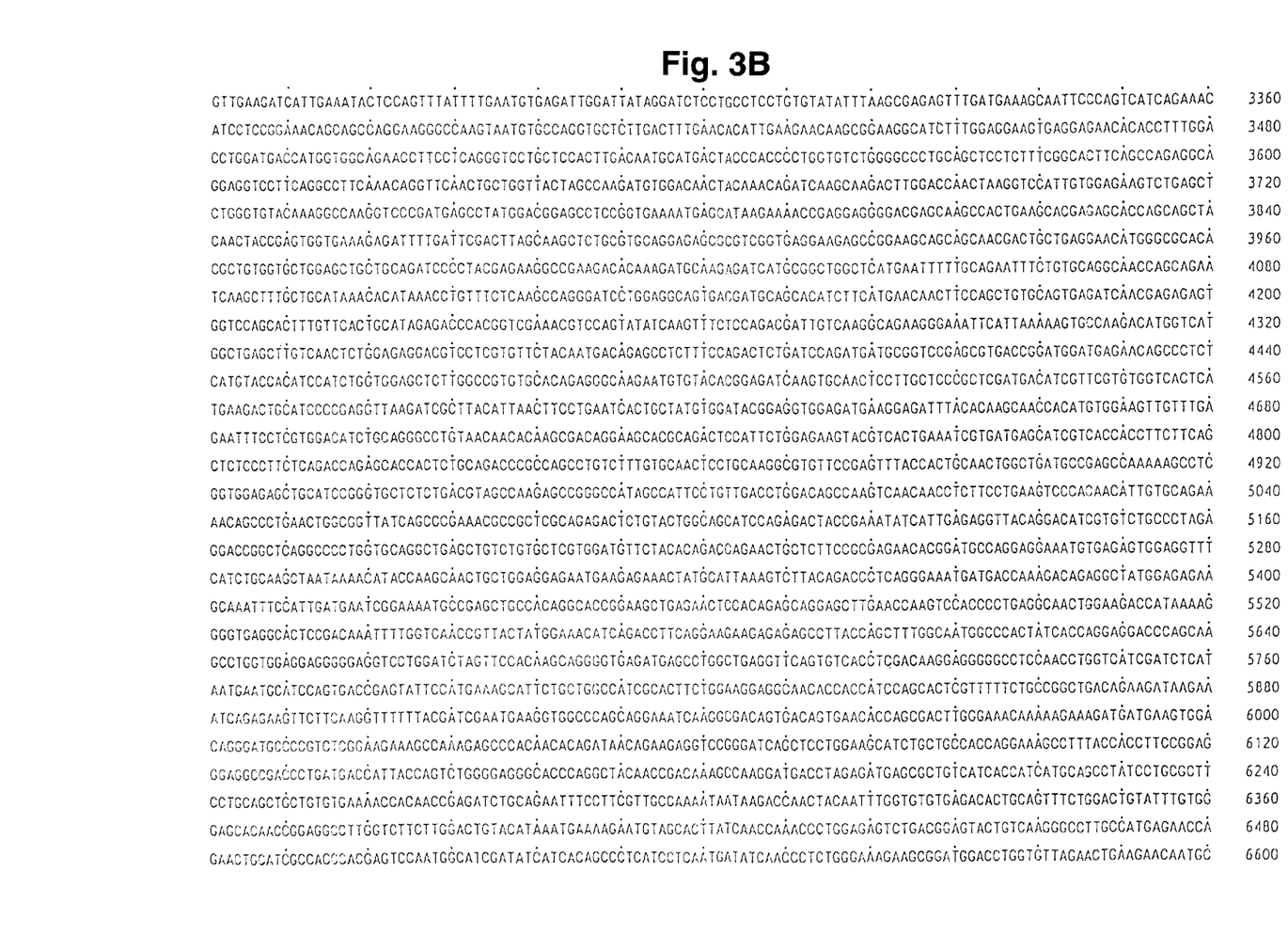
Figure 3C:
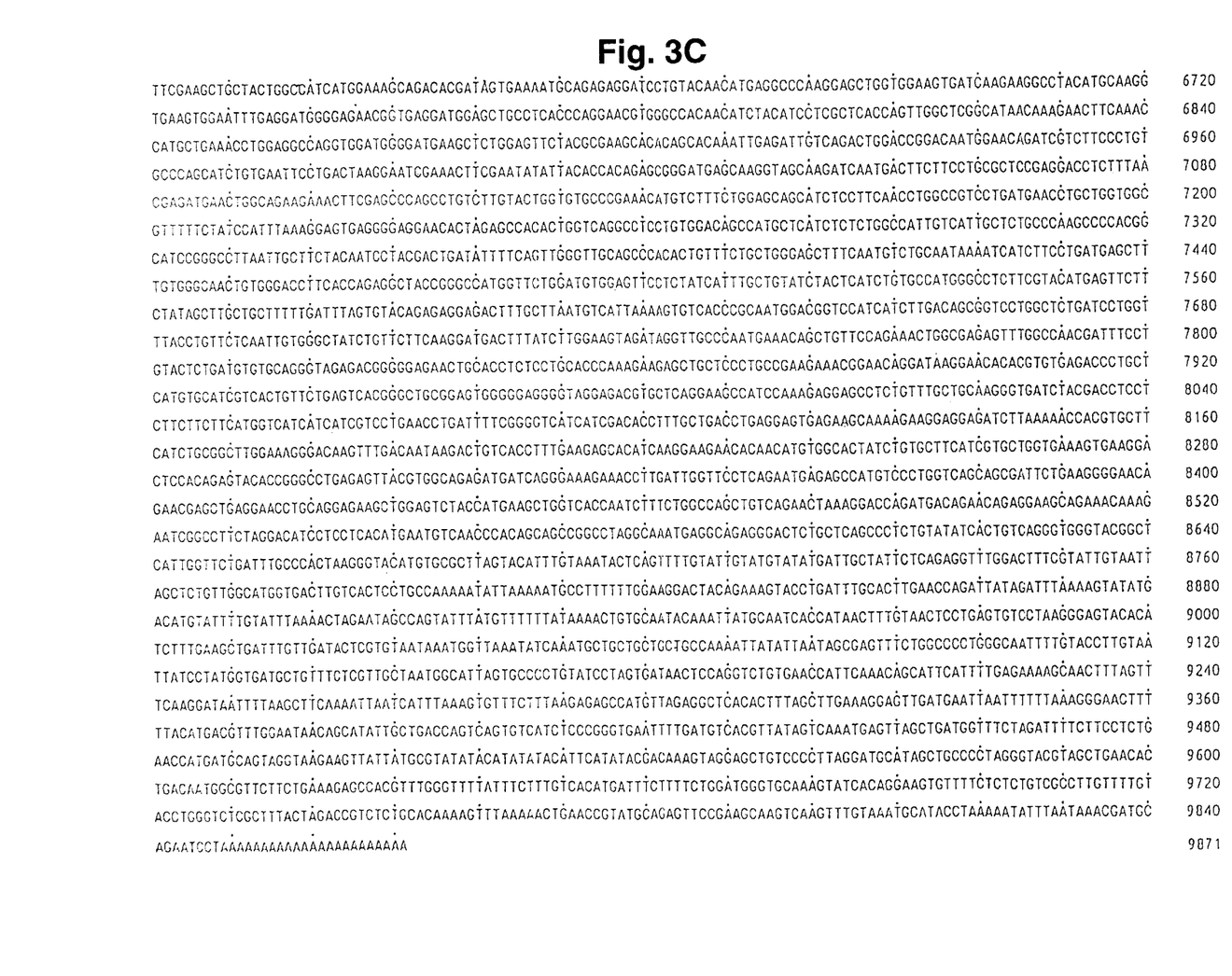

The recombinant plasmid according to the invention comprises a DNA coding for the polypeptide specified by the amino acid sequence shown in FIGS. 2(*a*), 2(*b*) and 2(*c*) and a vector DNA. The vector DNA to be used may be any vector DNA provided that the genetic information of the DNA inserted in the resulting recombinant plasmid can be expressed in cells and the desired polypeptide can be produced thereby in significant amounts. As a preferred example, there may be mentioned pβact-CAT9 [N. Fregien et al., Gene, 48, 1 (1986)].

As a specific example of the recombinant plasmid, there may be mentioned pβact-C1 described in Example 5. A strain of *Escherichia coli* harboring pβact-C1, designated as *Escherichia coli* pβactP400C1, has been deposited since Dec. 1, 1989 with the Fermentation Research Institute, Agency of Industrial Science and Technology, Japan, under the accession number FERM BP-2668, in accordance with the Budapest Treaty.

The cells to be used in the practice of the invention may be either prokaryotic cells or eukaryotic cells provided that they can stably hold the recombinant plasmid introduced therein and the genetic information of the DNA insert can be expressed and the desired polypeptide produced in significant amounts. As the prokaryotic cells, there may be mentioned *Escherichia coli,* and *Neurospora crassa,* among others. As the eukaryotic cells, there may be mentioned *Saccharomyces cerevisiae,* NG108-15 cells, L cells, PC12 cells and NIH3T3 cells, for instance. Particularly, NG108-15 cells are preferred.

The above-mentioned DNA, recombinant plasmid and tranformant can be produced in the following manner.

1. Preparation of mouse cerebellum-derived cDNA library using λgt11

The cerebellum is isolated from mice of 2 to 3 weeks of age and immediately frozen. The frozen cerebellum is crushed and ribonucleotide, or ribonucleic acid (hereinafter referred to as "RNA", is extracted by the guanidinium-cesium chloride (CsCl) method [T. Maniatis et al., Molecular Cloning, A Laboratory Manual, 1982]. Then, poly $(A)^+$ RNA is purified by the oligo(dT)-cellulose method described in the reference cited above.

Then, the method of Gubler et al. [U. Gubler et al., Gene, 25, 263 (1982)] is used to prepare cDNA and prepare a cDNA library by introducing the cDNA into the vector λgt11 [T. V. Huynh et al., DNA Cloning Techniques, A Practical Approach, 49–78, IRL Press, Oxford, 1985].

It is preferable that, in the cDNA preparation mentioned above, the poly(A) RNA be gently placed on a 15% to 30% sucrose density gradient in a centrifuge tube and subjected to ultracentrifugation and a poly(A) RNA fraction with a sedimentation coefficient of not less than 23S be used so that a high-molecular-weight cDNA library can be constructed.

2. Cloning of cDNA for IP3-binding polypeptide cDNA for the polypeptide having IP3-binding ability can be cloned from the cDNA library constructed as described above in section 1 by screening by the above-mentioned method of Huynh et al. using monoclonal antibodies, 10A6, 18A10 and 4C11, prepared against P400 [N. Maeda et al., Shinkei Kagaku (Bulletin of the Japanese Neurochemical Society), 27, 60 (1988)].

3. Construction of recombinant plasmid and of transformed cells

The thus-cloned cDNA for the IP3-binding polypeptide can be introduced into a vector enabling the expression of the polypeptide in animal cells, preferably the vector pβact-CAT9 [N. Fregein et al., Gene, 48, 1 (1986)], whereby it becomes possible for the IP3-binding polypeptide to be expressed in animal cells.

The reaction conditions to be employed in the recombinant DNA techniques for the above-mentioned expression are generally as follows.

The digestion of DNA with a restriction enzyme is generally carried out using 0.1 to 20 μg of DNA in a reaction solution containing 2 to 200 mM (preferably 10 to 40 mM) Tris-HCl buffer (pH 6.0 to 9.5, preferably 7.0 to 8.0), 0 to 200 mM NaCl and 2 to 20 mM (preferably 5 to 10 mM) $MgCl_2$ in the presence of 0.1 to 100 units (preferably 1 to 3 units), per μg of DNA, of the restriction enzyme at 20 to 70° C. (the optimum temperature depending on the restriction enzyme used) for 15 minutes to 24 hours. The reaction is stopped generally by heating at 55 to 75° C. for 5 to 30 minutes. The reaction may also be stopped by deactivating the enzyme using such a reagent as phenol or diethyl pyrocarbonate. DNA fragments produced by restriction enzyme digestion can be purified, for example by low gelation temperature agarose gel electrophoresis (LGT method)[L. Wieslander, Analytical Biochemistry, 98, 305 (1979)].

The ligation of DNA fragments is carried out in a reaction solution containing 2 to 200 mM (preferably 10 to 40 mM) Tris-HCl buffer (pH 6.1 to 9.5, preferably 7.0 to 8.0), 2 to 20 mM (preferably 5 to 10 mM) $MgCl_2$, 0.1 to 10 mM (preferably 0.5 to 2.0 mM) ATP and 1 to 50 mM (preferably 5 to 10 mM) dithiothreitol (hereinafter referred to as "DTT") in the presence of 0.3 to 10 units of T4 DNA ligase at 1 to 37° C. (preferably 3 to 20° C.) for 15 minutes to 72 hours (preferably 2 to 20 hours).

For preparing a membrane fraction containing the expressed polypeptide from cultured transformant cells, cells cultured are recovered, washed with ice-cooled Tris-buffered physiological saline, suspended in ice-cooled buffer A containing 0.25M sucrose, 10 mM Tris-HCl buffer (pH 8.0), 0.1 mM ethylenediaminetetraacetic acid (hereinafter referred to as "EDTA"), 1 mM phenylmethylsulfonyl fluoride (PMSF), 0.01 mM pepstatin and 0.2 U/ml aprotinin, and homogenized by means of an ice-cooled glass-Teflon portable homogenizer (at 10 strokes at 1,000 rpm). Centrifugation is performed at about 3,000×g for 3 minutes at 2° C. to thereby remove nuclei. The supernatant is further centrifuged at 10,000×g for 5 minutes at 2° C., whereby a membrane fraction can be obtained as the sediment and a soluble fraction as the supernatant. The IP3-binding polypeptide can be recovered from the membrane fraction.

The following examples further illustrate the invention.

EXAMPLE 1

Construction of Mouse Cerebellum cDNA Library (1) Preparation of mouse cerebellum-derived mRNA The cerebella were excised from mice of 2 to 3 weeks of age and immediately frozen. One gram of the frozen cerebella was crushed and solubilized by addition of 10 ml of a solution containing 4M guanidine thiocyanate, 10 mM EDTA, 25 mM Tris-HCl buffer (pH 7.4), 1% (v/v) 2-mercaptoethanol and 2% (v/v) sodium lauroylsarcosinate. The solubilization product was transferred to a centrifuge tube and centrifuged at a low velocity (5,000 rpm, 15 minutes). The supernatant was layered onto 3 ml of a solution comprising 5.7M CsCl and 0.1M EDTA (pH 7.5) and centrifuged at 32,000 rpm and 20° C. for 18 hours using a Hitachi model RPS-40T rotor, whereby an RNA fraction was recovered as the sediment. The RNA sediment was dissolved in 2 ml of a solution containing 10 mM Tris-HCl buffer (pH 7.5), 5 mM EDTA and 1% (v/v) sodium laurylsulfate. After extraction with phenol and chloroform, the RNA was recovered by precipitation with ethanol. One milligram of the RNA obtained was dissolved in 1 ml of a solution containing 10 mM Tris-HCl buffer (pH 8.0) and 1 mM EDTA. The solution was incubated at 65° C. for 5 minutes and then 0.1 ml of 5M NaCl was added. The mixture was subjected to oligo(dT)-cellulose column (P-L Biochemicals) chromatography (column volume 0.5 ml). Elution of the poly(A)-containing RNA (mRNA) fraction adsorbed with a solution containing 10 mM Tris-HCl buffer (pH 8.0) and 1 mM EDTA gave about 100 μg of mRNA.

(2) cDNA synthesis

About 10 μg of the mRNA prepared as described above and 4 μg of oligo $(dT_{12-18})$ (Takara Shuzo) were dissolved in 98.4 μl of a solution containing 50 mM Tris-HCl buffer (pH 8.3), 8 mM $MgCl_2$, 30 mM KCl, 10 mM DTT, 1 mM each of dNTPs (dATP, dTTP, dGTP and dCTP), 10 μCi α-[$^{32}$P]dCTP and 60 units of ribonuclease inhibitor, 40 units of reverse transcriptase (Seikagaku Kogyo) was added, and incubation was conducted at 42° C. for 3 hours for the synthesis of DNA complementary to the mRNA. The reaction mixture was extracted with phenol and chloroform and then subjected to precipitation with ethanol, whereby about 15 μg of RNA-DNA double strands were recovered. The entire amount of the precipitate was dissolved in 95 μl of a solution containing 20 mM Tris-HCl buffer (pH 7.4), 5 mM $MgCl_2$, 10 mM $(NH_4)_2SO_4$, 5 μg bovine serum albumin (BSA), 0.1M KCl, 1 mM each of dNTPs (dATP, dTTP, dGTP and dCTP) and 1 μCi α-[$^{32}$P ]dCTP, 2 units of RNase H (Takara Shuzo) and 12 units of DNA polymerase I (Takara Shuzo) were added, and incubation was performed at 12° C. for 1 hour and then further at an elevated temperature of 22° C. for 1 hour for DNA-DNA double strand synthesis. The above reaction was stopped by adding EDTA and the reaction mixture was subjected to extraction with phenol and chloroform and then to precipitation with ethanol, whereby about 10 μg of a precipitate was recovered. To render the termini of the above double-stranded DNAs blunt, the whole amount of the precipitate was dissolved in 49 μl of a solution containing 33 mM Tris-HCl buffer (pH 7.9), 66 mM potassium acetate, 10 mM magnesium acetate, 0.5 mM DTT, 5 μg BSA and 0.1 mM each of dNTPs (dATP, dTTP, dGTP and dCTP), 4 units of T4 polymerase (Takara Shuzo) was added, and incubation was performed at 37° C. for 30 minutes. Then, 2.4 units of DNA polymerase I Klenow fragment (Takara Shuzo) was added, and incubation was conducted at room temperature for 10 minutes. The reaction was stopped by addition of EDTA, which was followed by extraction with phenol and chloroform. Ethanol precipitation gave about 9 μg of reaction product.

Then, for methylating the DNA double strands at the EcoRI (restriction enzyme) cleavage site, the whole amount of the above reaction product was dissolved in 49 μl of a solution containing 100 mM Tris-HCl buffer (pH 8.0), 1 mM EDTA, 5 mM DTT and 0.15 mM S-adenosyl-L-methionine, 100 units of EcoRI methylase (Takara Shuzo) was added, and incubation was performed at 37° C. for 1 hour. The reaction mixture was extracted with phenol and chloroform, and the reaction product (about 7.5 μg) was recovered by ethanol precipitation.

For joining an EcoRI linker to the reaction product, the whole amount of the above reaction product was dissolved in 37 μl of a solution containing 66 mM Tris-HCl buffer (pH 7.6), 6.6 mM MgCl$_2$, 10 mM DTT, 40 μg EcoRI linker (Takara Shuzo) and 1 mM ATP, 1,050 units of T4 ligase (Takara Shuzo) was added, and incubation was performed at 12° C. for 16 hours. NaCl was then added to a final concentration of 100 mM, incubation was performed at 65° C. for 10 minutes, then 60 units of EcoRI (Takara Shuzo) was further added, and incubation was performed at 37° C. for 2 hours. The reaction was stopped by adding EDTA, which was followed by extraction with phenol and chloroform. Ethanol precipitation gave about 6 μg of the desired cDNA.

(3) Construction of λgt11 library

For inserting the above cDNA (with EcoRI linkers on both ends) into the λgt11 vector at the EcoRI cleavage site to give a cDNA library, the above-mentioned method of Huynh et al. [T. Huyunh et al., DNA Cloning Techniques, A Practical Approach, 49–78, IRL Press, Oxford (1985)] was used. Thus, the λgt11 vector (Promega) was cleaved with EcoRI and deprived of the phosphate residue from the cleavage site, and the above-mentioned cDNA was joined thereto at the EcoRI cleavage site. A λgt11 library was constructed by introducing the ligation mixture into a λ phage packaging kit [Strategene's Giga Pack Gold].

EXAMPLE 2

Construction cDNA Library using High-Molecular-Weight RNA Fraction

A cDNA library was constructed in the same manner as in Example 1 except that a fraction consisting of molecules showing a sedimentation coefficient not smaller than 23S as obtained by further subjecting the mRNA used in Example 1 to sucrose density gradient centrifugation was used as a high-molecular-weight RNA fraction and that, in cDNA synthesis, a random hexamer mixture (Pharmacia Fine Chemicals) was used in lieu of oligo(dT)$_{12-18}$.

EXAMPLE 3

Cloning of cDNA for IP3-binding polypeptide

The high-molecular-weight RNA fraction-derived cDNA library prepared in Example 2 was subjected to screening by the method of Huynh et al. [T. Huynh et al., above] using three monoclonal antibodies, 10A6, 18A10 and 4C11, to IP3-binding P400 [N. Maeda et al., Shinkei kagaku (Bulletin of the Japanese Neurochemical Society), 27, 60 (1988)], followed by Western blot analysis, whereby five positive clones (23-2, 23-5, 23-9, 23-12S and 23-15) were selected out.

The cDNAs inserted in the λ phage vectors were prepared from the above five clones in the conventional manner by preparing phages, extracting DNAs and digesting the DNAs with EcoRI. Using these as probes, the cDNA library constructed in Example 1 was screened by the plaque hybridization technique, whereby 75 positive clones, including 5T1, 3T5, 6T14, 10T5, 7T15, 2C2 and 1C5, were obtained. To determine the base sequences of the cDNA portions inserted in these positive clones, they were subcloned in pUC118 and pUC119 (Takara Shuzo).

EXAMPLE 4

Construction of cDNA Coding for Full Length Polypeptide According to Invention and Determination of Base Sequence Thereof The base sequences of the cDNAs in the twelve clones 23-3, 23-5, 23-9, 23-12S, 23-15, 5T1, 3T5, 6T14, 10T5, 7T15, 2C2 and 1C5 obtained in Example 3 were determined by the method of Messing [J. Messing, Gene, 19, 269 (1982)]. By combining the base sequences thus found, the full length base sequence of the cDNA for the polypeptide according to the invention (FIGS. 3(*a*, 3(*b*) and 3(*c*)) and the entire amino acid sequence of said polypeptide (FIGS. 2(*a*), 2(*b*), and 2(*c*)) were determined. A unified cDNA was constructed from the above clones and inserted into pUC119 (Takara Shuzo). The resulting plasmid was named P400Cl.

EXAMPLE 5

Expression of Polypeptide According to Invention in NG108-15 cells pβact-CAT9 (5 μg) was dissolved in 50 μl of a solution containing 10 mM Tris-HCl buffer (pH 7.5), 7 mM MgCl$_2$ and 60 mM NaCl, 20 units of HindIII (Takara Shuzo) was added, and incubation was performed at 37° C. for 2 hours. The reaction was stopped by adding EDTA, the reaction mixture was extracted with phenol and chloroform, and DNA was recovered by ethanol precipitation. The whole amount of the reaction product (precipitate) was dissolved in 25 μl of a solution containing 50 mM Tris-HCl buffer (pH 7.5), 10 mM MgSO$_4$, 0.1 mM DTT and 0.1 mM each of dNTPs (dATP, dTTP, dGTP and dCTP), 4 units of DNA polymerase I Klenow fragment (Takara Shuzo) was added, and incubation was performed at room temperature for 30 minutes to render pβact-CAT9 blunt-ended at the HindIII cleavage site.

The above reaction was stopped by adding EDTA, which was followed by extraction with phenol and chloroform. The reaction product was recovered by ethanol precipitation and the whole amount thereof was dissolved in 50 μl of a solution containing 10 mM Tris-HCl buffer (pH 7.5), 7 mM MgCl$_2$, 100 mM KCl and 7 mM 2-mercaptoethanol. After adding 20 units of HpaI, the solution was incubated at 37° C. for 2 hours. EDTA was then added to stop the reaction. After extraction with phenol and chloroform, the reaction product was recovered by precipitation with ethanol.

One microgram of the above reaction product was dissolved in 20 μl of a solution containing 66 mM Tris-HCl buffer (pH 7.6), 17.5 pmol SalI linker (GGTCGACC: Takara Shuzo), 6.6 mM $MgCl_2$, 10 mM DTT and 0.5 mM ATP, 300 units of T4 DNA ligase (Takara Shuzo) was added, and incubation was performed at 12.5° C. for 16 hours. Then, NaCl was added to a final concentration of 150 mM, 50 units of SalI was added, and the reaction was performed at 37° C. for 3 hours. The reaction was stopped by adding EDTA. Ethanol precipitation following phenol-chloroform extraction gave a vecter DNA for the expression of the polypeptide according to the invention.

Then, a SalI linker was added to the whole length cDNA for the polypeptide according to the invention as prepared in Example 4 at each end thereof in the same manner as described above and inserted into the vector prepared above at the SalI site thereof to give pβact-C1.

The plasmid pβact-C1 thus obtained was introduced into NG108-15 cells [T. Amano et al., Exp. Cell. Res., 85, 399–408 (1974)] by the conventional calcium phosphate method [M. Miura et al., Gene, 75, 31 (1989)]. The expression of the polypeptide according to the invention was confirmed in the transformed cells.

In accordance with the invention, the polypeptide capable of binding to inositol 1,4,5-trisphosphate can now be supplied economically in large quantities.

While the invention has been described in detail and with reference to specific embodiments thereof, it will be apparent to one skilled in the art that various changes and modifications can be made therein without departing from the spirit and scope thereof.

Figure 1:
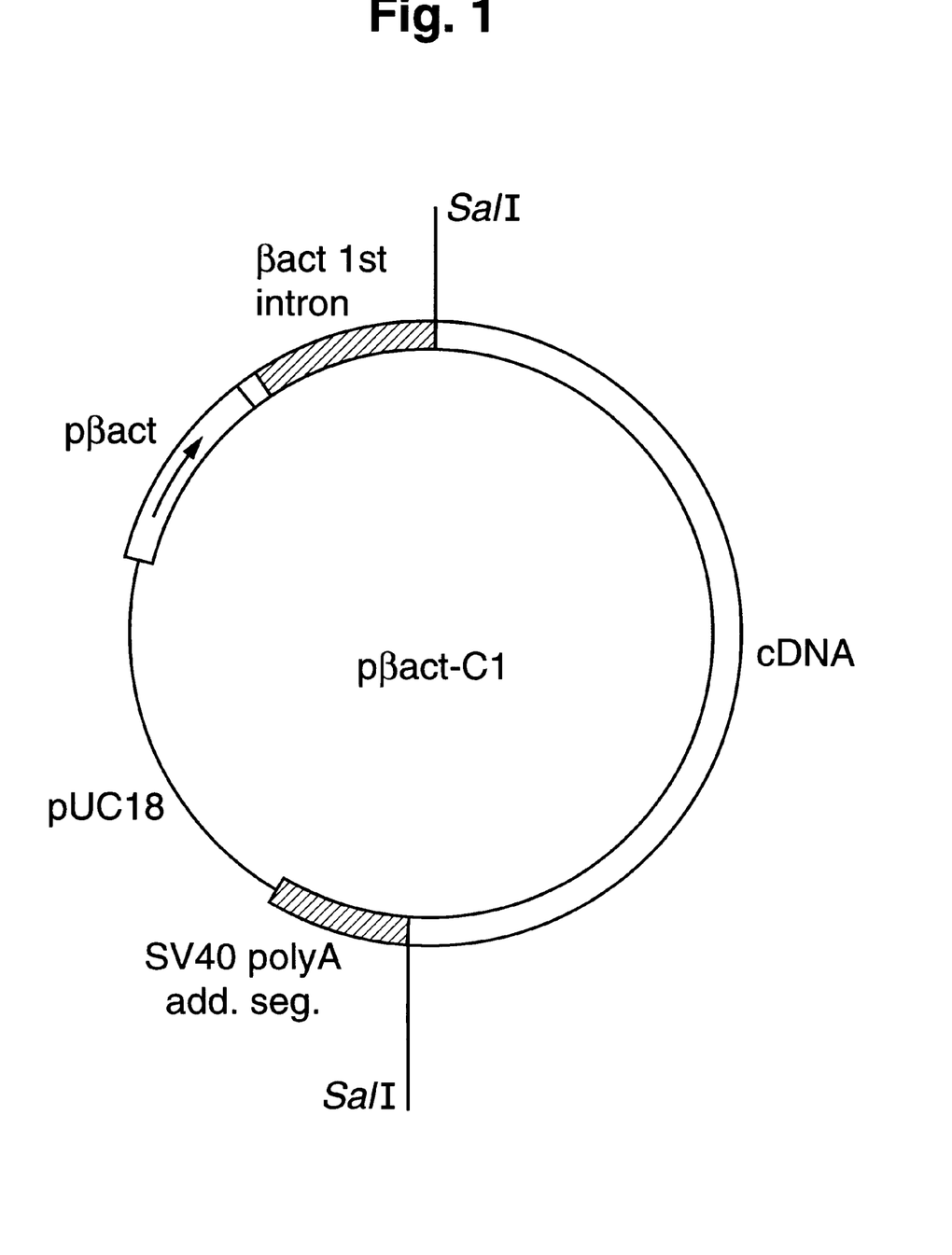
FIG. 1 shows a restriction enzyme map of the plasmid pβact-C1.

What is claimed is:

1. An isolated deoxyribonucleotide (DNA) coding for a polypeptide which contains the amino acid sequence shown in FIG. 1 and binds to inositol 1,4,5-trisphosphate.

2. The DNA as claimed in claim 1, said DNA containing the nucleotide sequence shown in FIG. 3.

3. A recombinant plasmid which comprises a vector DNA and a DNA coding for a polypeptide which contains the amino acid sequence shown in FIG. 2 and binds to inositol 1,4,5-trisphosphate.

4. The recombinant plasmid as claimed in claim 3, wherein the DNA coding for the polypeptide is a DNA containing the nucleotide sequence shown in FIG. 3.

5. A cell harboring a recombinant plasmid comprising a vector DNA and a DNA coding for a polypeptide which contains the amino acid sequence shown in FIG. 2 and binds to inositol 1,4,5-trisphosphate.

6. The cell as claimed in claim 5, wherein the DNA coding for the polypeptide is a DNA containing the nucleotide sequence shown in FIG. 3.

7. The cell as claimed in claim 5, said cell being a microbial or an animal cell.

* * * * *